(12) United States Patent
Hamilton

(10) Patent No.: US 8,277,825 B2
(45) Date of Patent: Oct. 2, 2012

(54) INSECT ATTRACTANTS AND THEIR USE IN METHODS OF INSECT CONTROL

(75) Inventor: James Gordon Campbell Hamilton, Cheshire (GB)

(73) Assignee: Keele University, Staffordshire (GB)

( * ) Notice: Subject to any disclaimer, the term of this patent is extended or adjusted under 35 U.S.C. 154(b) by 0 days.

(21) Appl. No.: 12/859,393

(22) Filed: Aug. 19, 2010

(65) Prior Publication Data

US 2010/0310620 A1 Dec. 9, 2010

Related U.S. Application Data

(63) Continuation of application No. PCT/GB2009/000474, filed on Feb. 20, 2009.

(60) Provisional application No. 61/029,956, filed on Feb. 20, 2008.

(30) Foreign Application Priority Data

Feb. 20, 2008 (GB) .................................. 0803153.6

(51) Int. Cl.
*A01N 25/00* (2006.01)
*A01N 37/00* (2006.01)
*A61K 31/20* (2006.01)
*A61K 31/201* (2006.01)
*A61K 31/202* (2006.01)

(52) U.S. Cl. ........................................ 424/405; 514/558

(58) Field of Classification Search .................. None
See application file for complete search history.

(56) References Cited

U.S. PATENT DOCUMENTS

| 3,996,348 | A | * | 12/1976 | Greenberg | .................... 424/409 |
| 4,774,234 | A | | 9/1988 | Puritch et al. | |
| 4,944,734 | A | * | 7/1990 | Wallach | ........................ 604/358 |
| 2006/0041018 | A1 | | 2/2006 | Hamilton et al. | |

FOREIGN PATENT DOCUMENTS

| EP | 0 583 774 A1 | 2/1994 |
| EP | 1 787 514 A1 | 5/2007 |
| JP | 63-188327 | 12/1988 |
| JP | 05-295278 | 9/1993 |
| JP | 07-238003 | 12/1995 |
| JP | 2004-283106 | 10/2004 |
| KR | 1995-0005428 | 5/1995 |
| WO | WO 94/19947 | 9/1994 |
| WO | WO 2007/039215 | 4/2007 |

OTHER PUBLICATIONS

Byrne & Bellows—Whitefly Biology, Annu. Rev. Entomol. 1991. 36:431-57.
Csizinszky et al—Evaluation of color mulches and oil sprays for yield and for the control of silverleaf whitefly, *Bemisia argentifolii* (Bellows and Perring) on tomatoes. Crop Protection 1997, vol. 16, No. 5, pp. 475-481.
Doff Portland Ltd—Safety Data Sheet, Jul. 2004.
Nelson et al—The composition of external lipids from adult whiteflies, *Bemisia tabaci* and *Trialeurodes vaporariorum*. Comp. Biochem, Physiol. 109B, 1994, pp. 293-303.
OECD—Guidance for Registration Requirements for Pheromones and Other Semiochemicals Used for Arthropod Pest Control. OECD Environment, Health and Safety Publications, Series on Pesticides No. 12, 2001.

* cited by examiner

*Primary Examiner* — Ernst Arnold
(74) *Attorney, Agent, or Firm* — Woodard, Emhardt, Moriarty, McNett & Henry LLP

(57) ABSTRACT

The present invention utilizes a fatty acid as an attractant in a method of attracting whiteflies. By using a fatty acid as a whitefly attractant, it is possible to attract whiteflies to a desired location. The fatty acid can be used in a lure or other propagator to provide a dispersion of fatty acid in the air, the variation in the concentration of the fatty acid in the air being such that a whitefly is attracted to the lure as the source of the fatty acid. The use of a fatty acid as an attractant results in significantly higher levels of attraction, as measured by the number of whiteflies attracted to a sticky trap, as compared to the use of color alone.

25 Claims, No Drawings

INSECT ATTRACTANTS AND THEIR USE IN METHODS OF INSECT CONTROL

CROSS-REFERENCE TO RELATED APPLICATIONS

This application is a continuation of International Application No. PCT/GB2009/000474, filed Feb. 20, 2009, which claims priority from Great Britain Patent Application No. 0803153.6, filed Feb. 20, 2008, and from U.S. Provisional Patent Application No. 61/029,956, filed Feb. 20, 2008, all of which are hereby incorporated herein by reference.

FIELD OF THE INVENTION

The present invention is concerned with methods of attracting, monitoring and controlling whiteflies using fatty acids as attractant pheromones. In particular, the present invention is concerned with propagators comprising a fatty acid and their use in methods of attracting whiteflies to a whitefly monitoring device or a whitefly killing device.

BACKGROUND TO THE INVENTION

Amongst the many insect pests that are harmful to crops, Aleyrodidae (hereinafter whiteflies) represent a particular concern for growers, both in the UK and elsewhere. Indigenous and now established (formerly non-indigenous) whitefly species in the UK include Glasshouse whitefly (*Trialeurodes vaporariorum/T. vap*) and *Bemisia afer*. Current non-indigenous whitefly species of major concern include Tobacco whitefly (*Bemisia tabaci/B. tabaci*), *Trialeurodes ricini* and *Trialeurodes abutiloneus*.

*B. tabaci* is a worldwide pest and virus vector. Originally known as a pest of sub-tropical crops, the species is now widely distributed under glass in temperate areas including most of Europe. It is not established in the UK but it could establish in protected environments, where it has the potential to be a major pest, particularly of glasshouse salad crops such as tomato and cucumber.

*B. tabaci* is a major vector of more than 110 virus species. In the UK, the risk of virus transmission presents a serious threat to protected crops, particularly vegetables. *B. tabaci* is a pest of an extremely wide range of host plants, and the number of recorded hosts is increasing. They include crops grown outside in the tropics and sub-tropics (including cotton, soyabean and cassava), vegetable and salad crops grown under glass in Europe (e.g. cucumber, aubergine, peppers and tomatoes) and ornamental plants (e.g. poinsettia).

Approximately 125 plant viruses, many of them causing potentially significant or devastating diseases, are transmitted by whiteflies, of which *B. tabaci* (approximately 110 viruses) is by far the most important vector. By contrast, *Trialeurodes* species transmit very few viruses and *Bemisia afer* only one.

*B. tabaci* and *T. vap* can be found on the upper and lower surfaces of leaves of crops grown in glasshouses. The adults feed on growing shoots and lay eggs that hatch into tiny white scales that remain attached to the underside of leaves. Direct damage to plants by *B. tabaci* and *T. vap* is caused by feeding activity and subsequent virus transmission. Indirect damage occurs due to contamination of leaves with honeydew, on which sooty mould develops and intercepts light, thereby reducing photosynthesis.

A major issue for growers can be damage to unripe crops which are exported where damage is not visible before ripening and not detectable until arrival at the target market.

Whitefly can be difficult to control because they have a very fast lifecycle. Any control method must be implemented early and regularly to control severe or early outbreaks.

Naturally, any efforts at controlling or containing whiteflies will be greatly enhanced if the particular whitefly species present can be identified. Indeed, the identification of indigenous and, potentially, non-indigenous whitefly species is an important precursor to the exclusion, containment, and eradication or control of these invertebrate pests and the viruses that they transmit.

A number of approaches to the identification and monitoring of whitefly species are known, with the trapping of whitefly being the most common. A well known whitefly trap (also suitable for use with other insect pests) is the Yellow Sticky Trap (YST), available from Agrisense-BCS Ltd. These traps comprise an adhesive applied to a plastic backing sheet. The backing sheet is coloured yellow so as to attract whiteflies. The backing sheet may be printed with a grid to assist in the counting of whiteflies. Typically the traps are suspended above the crop.

Such traps can also be used for monitoring and/or controlling other insects. For certain insects other than whiteflies, pheromones can be added to the trap to further increase the degree of attraction. An example of the application of an insect pheromone to a sticky trap is disclosed in US2006/0041018, wherein isobornyl-containing compounds are proposed as pheromones for monitoring and/or controlling *Thysanoptera* (thrips).

However, in the case of whiteflies, no attractant pheromone is available. Indeed no whitefly pheromones have been identified. In this connection, a compound that is a pheromone for one particular family of insects would not be expected to be a pheromone in respect of a different family, so it is not effective to use pheromones for other insects. This means that the control and monitoring of whiteflies presently relies on conventional trapping methods wherein colour (typically yellow) represents the only means of attraction.

In addition to traps, a physical barrier in the form of insect mesh (as available from Harold Horticulture) can reduce the number of whitefly attacks. A further approach is to plant a trap crop, which is more attractive to whiteflies than the crop itself. These can be planted between the crop (row intercropping) or around the crop (perimeter trap crop). An example of a trap crop is squash. A further related approach is to grow plants between the crop that naturally repel whiteflies, for example French Marigolds (*Tagetes patula*).

Biological control measures include the introduction of one or more natural predators selected from *Encarsia formosa* (parasitic wasp); *Delphastus catalinae* (parasitic ladybeetle); *Eretmocerus eremicus* (parasitic wasp—available for release in the UK under licence from DEFRA); *Macrolophus caliginosus* (predatory mind bug); *Amblyseius swirskii* (predator mite); *Verticillium lecanii* (a mycoinsecticide available as Mycotal from Plant Solutions Ltd); and *Beauveria bassiana* (a mycoinsecticide available as Naturalis-L from Troy Biosciences).

Chemical control measures include systemic insecticides such as imidacloprid, thiacloprid and azadirachtin. Azadirachtin is available in commercial preparations Neemix™ and Bioneem™.

Given the considerable problem posed by whiteflies and the potential for harm if *B. tabaci* were to become established, there is a need for an improved approach to the monitoring and control of whiteflies.

DESCRIPTION OF PREFERRED EMBODIMENTS

The present invention is based on the surprising discovery by the inventor that whiteflies are attracted to fatty acids. At its most general, the present invention proposes that fatty acids are used as an attractant pheromone to attract whiteflies in methods of attracting, monitoring, killing, controlling or modifying the behaviour of whiteflies. In addition that fatty acids can be incorporated into a lure or other propagator to attract whiteflies to a desired location, for example a trap.

Without wishing to be bound by theory, it is thought that the aliphatic chain of the fatty acid provides volatility such that the fatty acid can act as a chemical messenger through the air and the polar end group interacts with a whitefly receptor.

Whilst variation in the structural features of the fatty acid may be used to adjust the effectiveness of the fatty acid as an attractant pheromone for a particular species of whitefly, for all whitefly species a fatty acid will be an attractant pheromone. It is thought that this reflects similarities between the receptors of different whitefly species such that the generic fatty acid functionality provides an attractant pheromone response for all species, even if the magnitude of the response may vary between species and as a function of the structure of the fatty acid. Thus, the contribution made by the present invention has general applicability for all species of whiteflies.

In a first aspect, the present invention provides the use of a fatty acid as an attractant in a method of attracting whiteflies.

By using a fatty acid as a whitefly attractant, the present inventor has found that it is possible to attract whiteflies to a desired location. The fatty acid can be used in a lure or other propagator to provide a dispersion of fatty acid in the air, the variation in the concentration of the fatty acid in the air being such that a whitefly is attracted to the lure as the source of the fatty acid. In particular, the present inventor has found that the use of a fatty acid as an attractant results in significantly higher levels of attraction, as measured by the number of whiteflies attracted to a sticky trap, as compared to the use of colour alone.

The method of attracting whiteflies can be carried out in several ways. Typically the fatty acid is propagated or broadcast within an area infested (or potentially infested) by whitefly. This can be achieved by using a lure or other propagator comprising a fatty acid. Suitable propagators are discussed below.

The ability to attract whiteflies makes it possible to monitor, kill, control and modify the behaviour of whiteflies and preferably the use includes use in such methods.

In particular, by causing whitefly to move from one location to another, it is possible to monitor whitefly numbers and/or whitefly species. In preferred embodiments the method of monitoring includes counting the number of whiteflies. Suitably the method includes identifying the species of whitefly.

This is an important advantage in establishing the threat posed by whiteflies and it can provide an early warning as to rising whitefly numbers. Improved monitoring using a fatty acid as an attractant or pheromone can therefore lead to more effective treatment of whitefly, for example by early treatment.

In particular, the use of a fatty acid as an attractant preferably improves the sensitivity of traps for whitefly, particularly at low levels of infestation or in easily damaged crops in glasshouses. This then allows growers to identify the pest and introduce additional control measures before pest populations reach economically damaging levels. As a result of improved monitoring and appropriate early control measures, reduced amounts of conventional pesticides may be needed, with concomitant savings in cost to the grower and burden to the environment.

Indeed, there is current interest and legislative pressure to reduce the number of active ingredients used in pesticides and remove large numbers of insecticides from the market.

A further application of the discovery that fatty acids are whitefly pheromones is in a method of killing the whitefly. This can be achieved by luring the whitefly to a whitefly killing device. Suitable whitefly killing devices are discussed below.

In this embodiment the fatty acid is not acting as a pesticide or other toxic agent, but as an attractant and is suitably associated with a whitefly killing device (e.g. a sticky trap or water trap). Additionally or alternatively to the fatty acid attracting the whiteflies directly to a whitefly killing device, suitably the fatty acid can increase the activity of a whitefly so as to increase the likelihood of the whitefly encountering a whitefly killing device.

As well as discovering that fatty acids can be used to lure whiteflies to a whitefly killing device, the present inventor has also noted that fatty acids can be used to modify the behaviour of whiteflies. For example, a fatty acid can be used to attract whiteflies away from a crop or to disrupt normal communications between whiteflies. By providing fatty acids in an area infested (or potentially infested) with whitefly, the effect of the natural pheromones released by the whitefly may be overcome or "masked" such that the whitefly become "confused". For example, a "cloud" of fatty acid may be provided around a whitefly such that the whitefly is unable to find the source of the fatty acid. In this way, the whitefly may move in a random way.

By utilising fatty acids in this way, it is possible to control whiteflies, for example to limit the population of whiteflies in a particular crop growing area such as a glasshouse or polytunnel.

Suitably, the structure of the fatty acid can be adjusted to control the effectiveness of the fatty acid as a whitefly pheromone. Preferably the fatty acid is a long chain fatty acid. Preferably the fatty acid has a chain length of 14 to 22 carbons, more preferably 15 to 20 carbons and most preferably 16 to 18 carbons. A chain length of 16 carbons is preferred and a chain length of 18 carbons is particularly preferred.

The fatty acid can be branched or unbranched, saturated or unsaturated.

Particularly preferred fatty acids are palmitic acid (hexadecanoic acid), linoleic acid (cis, cis-9,12-octadecadienoic acid), octadecenoic acid (particularly oleic acid (cis-9-octadecenoic acid)), eicosatrienoic acid and stearic acid (octadecanoic acid).

Palmitic acid and linoleic acid are particularly preferred. Linoleic acid is the most preferred.

Two or more fatty acids can be used in combination. Preferably one, two, three or four fatty acids are used in combination.

In embodiments, only one fatty acid is used and it is selected from palmitic acid and linoleic acid. Preferably only linoleic acid is used.

In embodiments where palmitic and linoleic acids are used in combination, preferably linoleic acid is present at a higher concentration than palmitic acid. Suitably linoleic acid is present at a concentration at least twice that of palmitic acid, preferably at a concentration of at least 4 times that of palmitic acid, and more preferably at a concentration of at least 5 times that of palmitic acid.

In further embodiments, palmitic acid, linoleic acid, oleic acid and stearic acid are used in combination. In such embodiments, palmitic acid and linoleic acid are preferably each present at a higher concentration than each of oleic acid and stearic acid. Suitably palmitic acid and linoleic acid are each present at a concentration at least twice that of oleic acid and stearic acid, preferably at least 4 times the concentration, more preferably at least 10 times the concentration. Thus, palmitic acid and linoleic acid are preferably major components and oleic acid and stearic acid are minor components, with respect to the total amount of fatty acid.

This reflects the inventor's findings that amongst the fatty acids produced naturally by whiteflies, linoleic acid is the major component, followed by palmitic acid and then oleic acid and stearic acid in much lower amounts. By mimicking this distribution of naturally occurring fatty acids, it is thought that the effectiveness of a method of attracting whiteflies may be optimised.

Suitably the fatty acid, or mixture of fatty acids, is used without additives. Suitably, the fatty acid, or mixture of fatty acids, is not mixed with other active agents (although as discussed herein, the fatty acid can be mixed with an insecticide, wherein the fatty acid attracts the whitefly to the insecticide).

The present inventor has found that the attractant effect of a fatty acid can be achieved for extended periods of time by controlling the release of the fatty acid into the air. This can be achieved by using a propagator. A "propagator" is adapted to release a pheromone such as a fatty acid into the air, for example by evaporation. In this connection, it is irrelevant whether or not the released fatty acid has the effect of attracting (luring) whiteflies to the propagator. Thus, a propagator includes arrangements wherein fatty acid is released into the air for the purposes of changing the behaviour of whiteflies, for example by confusing them or randomising their movements, as well as arrangements wherein fatty acids are released such that a whitefly follows the trail of fatty acids to the propagator.

Suitably the fatty acid is provided in a propagator.

Suitable propagators are known to the skilled reader as "lures" and a large number of such lures are available commercially (for example, from Russell IPM).

Suitably the lure comprises a matrix and the fatty acid is dispersed within the matrix. Suitably the matrix is porous. Preferably the matrix is made of rubber, preferably natural rubber. However, the matrix may be made of materials other than rubber, for example plastics material such as polymers.

In another arrangement, the lure may be a laminate.

In another preferred arrangement, the lure is a container having fatty acid-permeable walls, wherein the container contains fatty acid. The container therefore provides a reservoir of fatty acid and a means for controllably releasing the fatty acid, i.e. via the permeable walls. Suitably the walls are flexible. Suitably the container is closed (or closable, for example with a closable opening) such that fatty acid can leave the container only via the walls. In preferred arrangements, the flexible walls are made from a plastics material, preferably polyethylene. In particularly preferred embodiments the container is a bag or sachet.

In a further preferred arrangement the lure is a container, preferably a tube, which contains fatty acid, wherein the container comprises an orifice through which the fatty acid can be released from the container. Suitably the container is closed (or closable, for example with a closable opening) such that fatty acid can leave the container only via orifice. The diameter of the orifice can be adjusted to control the rate of release (typically via evaporation) of the fatty acid. Suitable containers are Eppendorf tubes (centrifuge tubes) which have been adapted by providing an orifice in one of the walls of the tube.

In the methods, uses and compositions of the present invention, the fatty acid is preferably used in low concentrations to optimise the attractant pheromone effect. For example, the present inventor has found that <1 mg fatty acid when applied to a propagator attached to a sticky trap is sufficient to attract whiteflies to the sticky trap over a period of many days or weeks.

Preferably the propagator is adapted to release fatty acid in an amount which is at least the same as the amount of fatty acid produced by a single whitefly. Suitably the propagator releases an amount that is at least twice the amount produced by a single whitefly, preferably at least four times, more preferably at least 8 times and more preferably at least 20 times the amount produced by a single whitefly. The preferred release rate from the propagator is in the range 1 to $10^6$ nanograms per hour, more preferably 10 to $10^5$ nanograms per hour and most preferably 20 to $10^4$ nanograms per hour.

The propagator is preferably associated with a whitefly killing device for immobilising and/or killing the whitefly, or with a whitefly monitoring device.

In this way, a propagator associated with a whitefly killing device may be used to attract whitefly and then immobilise or kill the whitefly so as to remove the whitefly from a crop growing area.

Suitably the whitefly killing device is a trap.

In a preferred embodiment, the trap comprises a substrate and a sticky adhesive coating applied to the substrate. Suitably the substrate is in the form of a sheet. Typically the sheet is rectangular. Preferably the sheet has dimensions of about 5 to 10 cm by about 10 to 15 cm, although other dimensions are possible. The substrate may also be in the form of an elongate strip.

Preferably the substrate comprises a plastics material, but it can also be made of paper or other materials. Preferably the sticky adhesive coating is non-toxic. Such adhesive coatings or "insect glues" are known and are typically polymeric. Traps of this sort are known as sticky traps, with yellow sticky traps (YSTs) being a preferred example.

In a preferred arrangement of this sort of trap, the propagator is integral with the trap. Indeed the trap is preferably also the propagator. Thus, suitably the substrate is porous to allow impregnation of a fatty acid. Alternatively or additionally, the fatty acid can be incorporated into the adhesive coating, e.g. by adding a fatty acid directly to the adhesive coating or by formulating the adhesive with the fatty acid prior to application to the substrate.

Thus, in such traps/propagators, one or both of the substrate and the sticky adhesive layer can act as a matrix in which the fatty acid is dispersed and from which it can evaporate under typical glasshouse or polytunnel conditions.

However, it is preferred that the propagator is not part of the trap. In such embodiments, the propagator is preferably attached to the trap.

In a second preferred embodiment, the trap comprises a container which in use is filled with a mixture of water and detergent. When a whitefly enters the trap, it will fall into the water-filled container and become immobilised on contact with the water. This type of trap is commonly known as a water trap.

Preferably the propagator is suspended above the container. Suitably the trap includes attachment means to which the propagator can be attached. In this way, whiteflies are attracted to the trap and brought into proximity with the water, thereby increasing the chances of immobilising the whiteflies. This sort of trap is particularly preferred because large numbers of whiteflies can be trapped.

Typically, the fatty acid is provided in a composition. Thus, in respect of each of the uses referred to above, the fatty acid may be present as a composition comprising a fatty acid.

Preferably in the use and methods described herein the fatty acid is provided in a whitefly attractant composition, wherein the whitefly attractant composition comprises, preferably substantially consists of, more preferably consists essentially of and most preferably consists of a fatty acid or mixture of fatty acids.

Alternatively, the fatty acid can be provided as a composition comprising an insecticide. The insecticide can be any one or more of the known insecticides. Preferably the insecticide is selected from azadirachtin, imidacloprid, and thiacloprid. For example, commercially available products such as Neemix™ and Bioneem™ (which contain azadirachtin) can be used. Other insecticides (and their commercially available formulation) include bifenthrin (Talstar 10WP), cyfluthrin (Tempo 2E; Decathlon 20WP), d-phenothrin (Sumithrin 2EC; PT 1400), fenpropathrin (Tame 2.4EC), fluvalinate (Mavrik 2F), permethrin (Pounce), resmethrin (SBP-1382; PT 1200), pyrethrum (Pyrenone; PT 1100; PT 1600A), fenvalerate (Pydrin), lambda-cyhalothrin (Scimitar 10WP), acephate (PT 1300; Orthene TTO), naled (Dibrom), sulfotepp (Plantfume 103), chlorpyrifos (Dursban 50WP, Duraguard), diazinon (PT 1500R Knox Out), methiocarb (PT 1700), endosulfan (Thiodan 2EC, 3EC, 50WP), kinoprene (Enstar 5E), fenoxycarb (Preclude, Precision), pyriproxyfen (Distance), oxythroquinox (Joust), abamectin (Avid 0.15EC), pymetrozine (Endeavor 50WG) and pyridaben (Sammite 75SP).

As discussed above, fatty acids are particularly effective as an attractant when present at low concentrations. Thus, when formulated as a composition for killing whitefly in combination with an insecticide, the fatty acid is suitably present at a concentration of <1 wt % based on total weight of the composition. Preferably the fatty acid is present at a concentration of <0.5 wt %, more preferably <0.1 wt %, more preferably <0.05 wt %, and most preferably <0.01 wt %. Preferably the fatty acid is present in an amount of at least $10^{-4}$ wt %.

Suitably the composition is a liquid.

Preferably the method of attracting whiteflies includes attracting whiteflies in a crop growing area.

Preferably the crop comprises one or more of cotton, soyabean, cassava, vegetable plants, salad plants (e.g. cucumber, aubergine, peppers and tomatoes) and ornamental plants (e.g. poinsettia). Particularly important from an economic point of view are *poinsettia, fuchsia, abutilon,* regal *pelargonium, gerbera, hibiscus, verbena, lantana* and *begonia.* Vulnerable nursery stock includes *lavatera, ceanothus, philadelphus, cestrum,* hardy *fuchsia, solanum, clematis* and *passiflora.*

Suitably the methods and uses of the present invention take place in an enclosed crop growing area such as a glasshouse or polytunnel.

Whilst the present invention has general applicability for all species of whitefly, it is particularly preferred that the whitefly is selected from *T. vap* and *B. tabaci.* Of these, *T. vap* is particularly preferred.

In a further aspect, the present invention provides the use of a fatty acid as an attractant in a method of monitoring whiteflies.

In a further aspect, the present invention provides the use of a fatty acid as an attractant in a method of killing whiteflies.

In a further aspect, the present invention provides the use of a fatty acid as an attractant in a method of modifying the behaviour of whiteflies.

In a further aspect, the present invention provides the use of a fatty acid as an attractant in a method of controlling whiteflies.

In a further aspect, the present invention provides the use of a fatty acid as an attractant in a method of treating a crop for whitefly infestation.

In further aspects, the present invention provides methods corresponding to each of the uses of a fatty acid discussed above.

In particular, in one such further aspect, the present invention provides a method of attracting whiteflies to a predetermined location, the method comprising the step of providing a fatty acid at the predetermined location. Suitably the fatty acid is provided in a propagator and the propagator is located at the predetermined location.

In a further aspect, the present invention provides a method of monitoring whiteflies, the method comprising the step of providing a whitefly monitoring device and a fatty acid associated with the whitefly monitoring device. Suitably the fatty acid is provided in a propagator, which is preferably attached to the whitefly monitoring device. Preferably the whitefly monitoring device is a trap, suitably a sticky trap.

In a further aspect, the present invention provides a method of killing whiteflies, the method comprising the step of providing a whitefly killing device and a fatty acid associated with the whitefly killing device. Suitably the fatty acid is provided in a propagator, which is preferably attached to the whitefly killing device. Preferably the whitefly killing device is a trap, suitably a sticky trap or water trap.

In a further aspect, the present invention provides a method of modifying the behaviour of whiteflies, the method comprising the step of providing a propagator comprising a fatty acid.

The present invention is also concerned with compositions for killing whiteflies. A composition for killing whiteflies suitably comprises an insecticide. The present inventor has found that the effectiveness of such a composition may be increased by including a fatty acid as an attractant, to encourage the whiteflies to contact the composition and hence the insecticide. Thus, in a further aspect, the present invention provides a composition for killing whiteflies, the composition comprising a fatty acid and an insecticide. Preferred insecticides and concentrations of fatty acids have been discussed above.

Such compositions can be used to treat a crop, for example by direct application of the composition to the crop. This may be achieved by spraying the crop with the composition. Thus, in a further aspect, the present invention provides the use of a fatty acid as an attractant in a method of treating a crop for whitefly infestation.

In a yet further aspect, the present invention provides a method of treating a crop comprising the step of applying a composition to the plants, wherein the composition comprises an insecticide and a fatty acid.

The present invention is also concerned with propagators, whitefly killing devices and whitefly monitoring devices which include a fatty acid.

Thus, in a further aspect, the present invention provides a propagator comprising a fatty acid. Preferably the propagator is a lure. Preferably the fatty acid is selected from palmitic acid, linoleic acid, octadecenoic acid, oleic acid, stearic acid and eicosatrienoic acid.

In a further aspect, the present invention provides a whitefly killing device comprising a fatty acid. Preferably the fatty acid is selected from palmitic acid, linoleic acid, octadecenoic acid, oleic acid, stearic acid and eicosatrienoic acid. Preferably the whitefly killing device comprises a propagator, preferably a lure.

In a further aspect, the present invention provides a whitefly monitoring device comprising a fatty acid. Preferably the fatty acid is selected from palmitic acid, linoleic acid, octadecenoic acid, oleic acid, stearic acid and eicosatrienoic acid. Preferably the whitefly monitoring device comprises a propagator, preferably a lure.

In a related aspect, the present invention provides a method of attaching a propagator comprising a fatty acid to a whitefly killing device or a whitefly monitoring device.

In a related aspect, the present invention provides a method of making a propagator comprising a fatty acid, wherein the method includes the step of applying a fatty acid to the propagator. Suitably the fatty acid is applied to the propagator with a solvent, such as hexane, to assist impregnation. However, the fatty acid can also be applied neat.

Suitably the method includes the step of providing an enclosure or envelope for the propagator to prevent release of the fatty acid. For example, the enclosure may be aluminium foil wrapped around the propagator. This retains the fatty acid in the propagator until the propagator is to be used, at which point the enclosure is removed.

In a related aspect, the present invention provides a method of releasing a fatty acid in a glasshouse or polytunnel using a propagator.

In a related aspect, the present invention provides a method of treating a crop for whitefly infestation, wherein the method includes the step of providing at least one whitefly killing device and a fatty acid associated with the whitefly killing device.

Preferably the whitefly infestation is *Trialeurodes vaporariorum* infestation, in which case the fatty acid is preferably selected from palmitic acid and linoleic acid. Suitably, both palmitic acid and linoleic acid are used.

Alternatively or additionally, the whitefly infestation is *Bemisia tabaci* infestation, in which case, the fatty acid is preferably selected from octadecenoic acid, eicosatrienoic acid, palmitic acid and linoleic acid. Preferably, octadecenoic acid is oleic acid. Preferably eicosatrienoic acid is cis, cis, cis-11, 14, 17-eicosatrienoic acid. Suitably all of octadecenoic acid, eicosatrienoic acid, palmitic acid and linoleic acid are used.

In a further aspect, the present invention provides a method of monitoring whiteflies, wherein the method includes the step of providing at least one whitefly monitoring device in association with a fatty acid.

Preferably the whitefly infestation is *Trialeurodes vaporariorum* infestation, in which case the fatty acid is preferably selected from palmitic acid and linoleic acid. Suitably, both palmitic acid and linoleic acid are used.

Alternatively or additionally, the whitefly infestation is *Bemisia tabaci* infestation, in which case, the fatty acid is preferably selected from octadecenoic acid, eicosatrienoic acid, palmitic acid and linoleic acid. Preferably, octadecenoic acid is oleic acid. Preferably eicosatrienoic acid is cis, cis, cis-11, 14, 17-eicosatrienoic acid. Suitably all of octadecenoic acid, eicosatrienoic acid, palmitic acid and linoleic acid are used.

Whilst the present invention contributes to the art the valuable understanding that whitefly pheromones comprise fatty acids, it is likely that changes in the structure of a fatty acid will influence the effectiveness of a fatty acid as a whitefly attractant pheromone. With that in mind, the present invention proposes that fatty acids and combinations of fatty acids that are particularly adapted as whitefly attractants can be identified by testing such fatty acids alone or in combination and measuring their effect as an attractant for whiteflies.

Thus, in a further aspect, the present invention provides a method of identifying a fatty acid whitefly attractant, the method comprising the steps of (i) providing a population of whiteflies in a first location; (ii) providing one or more fatty acids in a second location; and (iii) after a predetermined length of time, measuring the number of whiteflies that have moved from the first to the second location. In this way, a higher number of whiteflies having moved from the first to the second location, as compared to a control experiment, is indicative of activity as a whitefly pheromone.

Such a method can be repeated with different whitefly species to identify fatty acids that are particularly effective attractants for that species.

Suitably an olfactomoeter, for example as described herein, is used in such a method.

Any one or more of the aspects of the present invention may be combined with any one or more of the other aspects of the present invention. Similarly, any one or more of the features and optional features of any of the aspects may be applied to any one of the other aspects. Thus, the discussion herein of optional and preferred features may apply to some or all of the aspects. In particular, optional and preferred features relating to the nature of the fatty acid, whitefly species, crop, and fatty acid concentrations apply to all of the aspects. Furthermore, optional and preferred features associated with a method or use may also apply to a product, in particular a composition or device, and vice versa.

DEFINITIONS

"Whitefly" is the common name given to the insect family Aleyrodidae.

"Fatty acids" are compounds of the formula:

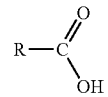

where R is a "fatty group" and is a $C_{1-30}$ alkyl group. The alkyl group, R, may be linear or branched, saturated or unsaturated. Typically, the alkyl group, R, is saturated, or is unsaturated. Where one or more ethylenic bonds (i.e., carbon-carbon double bonds) are present, they may be in a cis- or trans-conformation. The alkyl group is typically unsubstituted, but may be substituted with one or more substituents.

Conventionally, fatty acids are denoted "X:Y" where X is the number of backbone carbon atoms, including the carboxylic acid carbon atom, and Y is the number of ethylenic bonds. If ethylene bonds are present, their position and conformation (e.g., cis- and trans-) are usually indicated by a suitable prefix, c-, t-. If the conformation is not known, or is usually found as a mixture, it is usually denoted e-. If the unsaturation is acetylenic (triple bond) rather than ethylenic, it is usually denoted a-. If substituents are present, they too are usually indicated by a suitable prefix. Branched fatty acids are usually denoted as substituted linear fatty acids. For example, acetic acid ($CH_3COOH$) is a "2:0" fatty acid; butyric acid ($CH_3CH_2CH_2COOH$) is a "4:0" fatty acid; and oleic acid (cis-octadeca-9-enoic acid) is a "9c-18:1" fatty acid; isobutyric acid ($CH_3CH(CH_3)COOH$) is a "2-Me-3:0" fatty acid. See, for example, Robinson (1982), "Common Names and Abbreviated Formula for Fatty Acids," J. Lip. Res., Vol. 23, pp. 1251-1253.

Long-chain fatty acids, where R is $C_{8-30}$ alkyl, include the following: caprylic (8:0); pelargonic (9:0); capric (10:0); caproleic (9c-10:1); isolauric (10-Me-11:0); lauric (12:0); lauroleic (9c-12:1); myristic (14:0); myristoleic (9c-14:1); palmitic (16:0); palmitoleic (9c-16:1); stearic (18:0);

stearolic (9a-18:0); oleic (9c-18:1); linoleic (9c12c-18:2); linolenic (9c12c15c-18:3); elaidic (9t-18:1); arachidic (20:0); behenic (22:0); lignoceric (24:0); cerotic (26:0); montanic (28:0); and, melissic (30:0).

"Plants" and "crops" referred to herein includes a reference to each of the following: cotton, soyabean, cassava, vegetable plants, salad plants (e.g. cucumber, aubergine, peppers and tomatoes) and ornamental plants (e.g. *poinsettia, fuchsia, abutilon*, regal *pelargonium, gerbera, hibiscus, verbena, lantana, begonia, lavatera, ceanothus, philadelphus, cestrum*, hardy *fuchsia, solanum, clematis* and *passiflora*).

"Pheromones" are molecules that act as chemical messengers (semiochemicals) between members of the same species and are produced by members of that species. In particular, they trigger a behavioural response in a member of that species. "Attractant pheromone" as used herein refers to pheromones that prompt an individual to follow a trail of the pheromone towards the source of the pheromone.

The invention will now be further described with reference to the following examples.

EXAMPLES

Bioassay Apparatus

An olfactometer was used to test the effect of fatty acids on the behaviour of whiteflies.

The olfactometer comprised a Perspex® tube (295 mm long; 135 mm internal diameter). An end plate with a single centrally positioned hole was fixed at one end of the Perspex® tube. A removable end plate with a single hole in the centre was placed at the other end of the Perspex® tube.

A piece of yellow sticky trap (YST) was fitted over the fixed end plate. The YST had a hole (6 mm diameter) punched in the centre so that it aligned with the inlet hole in the removable end plate. During operation, cleaned air entered the olfactometer via the hole (inlet port) in the fixed end plate and left the olfactometer via the hole (outlet port) in the removable end plate.

Air was delivered to the olfactometer via cleaned Teflon® tubing (0.25 inch outer diameter) from a cylinder of compressed air. It was passed through two charcoal filters (to remove impurities) a rotameter (to regulate airflow) and a cleaned glass container (Dreschel bottle (DB)) before entering the olfactometer. The flow rate of air was set between 1 and 2 ml sec$^{-1}$.

The Teflon® tube passed into the olfactometer through the fixed end plate and through the hole in the YST and protruded by 4 mm into the olfactometer.

A modification to the above apparatus was made to allow the introduction of test samples into the bioassay apparatus. A short length of Teflon® tubing (4 cm) was placed between the DB and the Teflon® tubing leading to the inlet port of the olfactometer. A small hole was made in the tubing and a small piece of rolled-up filter paper (2 cm diameter filter paper disk) was placed inside the tubing under the hole.

Extract of whiteflies, solutions of synthetic chemicals or pure hexane (control chemical) were placed on the filter paper by inserting the needle of a syringe through the hole and injecting the chemicals directly onto the filter paper. The hole was sealed with Teflon® tape after the injection had been made. One syringe was dedicated for each test solution and control.

Preparation of Extracts

An extract of mixed age *T. vap* was prepared by removing 0.61527 g of *T. vap* from their rearing cages and adding 3 ml of double distilled hexane. Therefore 1 μl of the resulting solution comprised the extract of the equivalent of 204 μg of *T. vap*.

An extract of mixed age *B. tabaci* was prepared as for *T. vap* adult males and females. Adults were removed from cotton plants 4-5 days after they started to emerge, anaesthetised with $CO_2$ and placed in an 8 ml glass vial and clean hexane added (86.35 μg of *B. tabaci* per μl of solvent).

Derivatisation of *T. vap* Extract

In order to determine if the fatty acids might be responsible for the biological activity observed in the olfactometer, the fatty acids were derivatised by a saponification reaction to remove them from the extract.

Solutions of 5% $NaHCO_3$ and NaOH were prepared and excess added to two aliquots (200 μl) of *T. vap* extract. Controls were prepared in the same way with hexane instead of *T. vap* extract. After varying lengths of time up to 72 hours the hexane soluble fraction was removed and analysed by GC to determine the extent to which the fatty acid had been removed from the *T. vap* extract. It was found that the *T. vap* extracts to which 5% NaOH had been added reacted within 30 minutes. Whereas with the 5% $NaHCO_3$ solution 48 hours was required to ensure complete reaction. It was decided that given the less vigorous nature of the 5% $NaHCO_3$ reagent that the saponification would be completed with 5% $NaHCO_3$. The NaOH although efficient may have reacted with non-target molecules present (ketones, aldehydes, etc).

Example 1

GC Analysis of *T. vap* Crude Extract

*T. vap* crude extract prepared as described previously was analysed by gas chromatography on a 10 m×0.53 mm inner diameter HP-1 column Sample was introduced to the column via a heated (180° C.) split/splitless injector. The column was heated from an initial 40° C. after 1 minute to 150° C. at 10° C. $min^{-1}$ and held for 0.1 min before heating at 10° C. $min^{-1}$ to the final temperature of 250° C. The temperature was held isothermally at 250° C. for 20 minutes.

Two major peaks were observed; one at 19.74 minutes (16%) and the other at 21.46 minutes (84%). Minor peaks were observed at 19.52 minutes and 21.74 minutes.

Example 2

GC-MS Analysis of Crude *T. vap* Extract

1 μl of *T. vap* crude extract was analysed by GC-MS. The major component was found to be linoleic acid, the minor component palmitic acid. In addition trace amounts of oleic and stearic acid were found.

GC analysis with synthetic linoleic acid bought from Sigma Chemical Co. showed peak enhancement of the 21.48 minute peaks on co-injection of *T. vap* extract (0.1 μl) with linoleic acid (80 ng).

Comparison of peak areas between *T. vap* extract and linoleic acid standards indicated that 50 μl of *T. vap* extract placed on filter paper in the olfactometer studies contained 16-18 μg of linoleic acid. Based on an equivalence calculation the amount of palmitic acid in 50 μl of *T. vap* extract was 3.7 μg.

Example 3

GC Analysis of *B. Tabaci* Crude Extract

*B. tabaci* crude extract prepared as described previously was analysed by gas chromatography on a 10 m×0.53 mm inner diameter HP-1 column Sample was introduced to the column via a heated (180° C.) split/splitless injector. The column was heated from an initial 40° C. after 1 minute to 150° C. at 10° C. min$^{-1}$ and held for 0.1 min before heating at 10° C. min$^{-1}$ to the final temperature of 250° C. The temperature was held isothermally at 250° C. for 20 minutes.

Fatty acids present in *B. tabaci* (but not in *T. vap*) were tentatively identified as C18:1 octadecenoic acid (CAS 000112-62-9) and C20:3 eicosatrienoic acid (CAS 055682-88-7), as well as linoleic acid and palmitic acid. Mass spec analysis suggests that the octadecenoic is oleic acid and the eicosatrienoic acid is cis, cis, cis-11, 14, 17-eicosatrienoic acid.

Example 4

Laboratory Bioassay to Determine if Male *T. vap* are Attracted to Live Male and Female *T. vap*

Mixed age male and female (ca. 500) *T. vap* were removed from a bean plant and placed in a clean Drescher bottle (DB). Twenty five male *T. vap* were removed from the bean plant and placed on the base of the olfactometer in an 8 ml glass vial. Controls were no adult *T. vap* in the Drescher bottle. After 1 hour the numbers of whitefly caught on the YST were counted. The test was replicated 11 times the control 7 times.

The results indicated that the live adult *T. vap* were highly attractive (P=0.00028, 2-tailed T test) to male *T. vap*. The average % whitefly caught on the test sticky traps was 42.04% (±4.61%) whereas in the control experiments the average % whitefly caught was 13.68% (±3.83%).

Example 5

Laboratory Bioassay to Determine if Male *T. vap* are Attracted to Extract of Adult *T. vap*

Using the olfactometer (with modifications described above) an experiment was undertaken to determine the response of male *T. vap* to extract of adult male and female *T. vap*. The experiment was designed so that a solvent control was always followed by an extract test, 4 replicates were completed on each day (two controls and two tests). For the controls 50 μl of hexane was placed on the filter paper with a 10 syringe and the hole in the Teflon® tube sealed with a piece of Teflon® tape. After 30 minutes a further 50 μl of solvent was added to the filter paper. For the test 50 μl of extract (which was the equivalent of the extract of 10.2 mg of *T. vap*) was placed on the filter paper at the start of the replication and a further 50 μl added after 30 minutes. Again the number of whitefly on the YST were counted after 1 hour.

The data show that on average a significantly greater proportion of whitefly (44.8±3.08%) were caught on the test YST than on the control YST (18.93±2.98%) (P=0.000034, Paired T test).

Example 6

Laboratory Bioassay to Determine if Male *B. tabaci* are Attracted to Extract of Adult *B. tabaci*

Bioassays were undertaken as described for *T. vap*. 50 μl of *B. tabaci* extract was placed on filter paper in the inlet side of the olfactometer; an additional 50 μl of extract was added to the filter paper after 30 minutes. Twenty five lightly cooled adult male *B. tabaci* were placed inside the olfactometer and the number caught on the YST were recorded after 60 minutes. For controls hexane only was added to filter paper.

The results indicated a small but significant (P=0.0106) response to the YST when *B. tabaci* extract was present. 12% more male *B. tabaci* were caught on the YST when *B. tabaci* extract was present, as compared to the control.

Example 7

Bioassay of Saponified *T. vap* Extract

A bioassay was then undertaken with *T. vap* extract that had been derivitised with 5% NaHCO$_3$. 50 μl of the extract were added to the filter paper at the start of the bioassay and 50 μl were added after 30 minutes, in the same way as for the bioassays with the unmodified crude *T. vap* extract.

It was set up in the same way as with previous bioassays. Care was taken to ensure that the *T. vap* extract was maintained at the original concentration. GC-MS analysis was undertaken on the extract after saponification to determine how much fatty acid remained; this analysis revealed that the reaction had been complete and no fatty acids remained in the extract.

The results indicated that the biological activity was lost after the saponification reaction (NS, P=0.08, paired T test).

Example 8

Bioassay of Fatty Acids Identified by GC/MS Analysis

A solution of linoleic and palmitic fatty acid in the ratio suggested by the GC analysis of Example 2 was prepared so that a 10 μl aliquot contained 20 μg and 4 μg of the respective fatty acids. 10 μl of the solution was added to the bioassay at the start of the bioassay and 10 μl after 30 minutes.

The results indicated that the fatty acids were biologically active and attractive to *T. vap* (P=0.000065 Ttest paired).

Example 9

*B. tabaci* Response to *T. vap* Fatty Acids

The two fatty acids (linoleic and palmitic acid) which were shown to be attractive to *T. vap* were bioassayed with *B. tabaci*.

The fatty acids did not induce any response in the olfactometer bioassay (NS, P=0.296, paired T test). This suggests that one or more of the other fatty acids identified from the *B. tabaci* extract but not present in the *T. vap* extract may be required in order to provide a measurable response using the olfactometer bioassay. Indeed, the presence of one compound may assist the attractiveness of another without being attractive itself. Thus, as discussed above, the highest levels of attraction may be achieved when the fatty acid(s) used as a whitefly attractant is selected so as to mimic the fatty acid(s) produced by the particular whitefly species concerned.

The invention claimed is:

1. A method of attracting Aleyrodidae (hereinafter whiteflies), comprising exposing the whiteflies to a fatty acid composition comprising: a) the combination of palmitic acid, linoleic acid, oleic acid and stearic acid; or b) the combination of octadecenoic acid and eicosatrienoic acid; at a rate of $10^{-9}$ to $10^{-3}$ grams per hour.

2. A method according to claim 1, wherein the method further includes monitoring attracted whiteflies.

3. A method according to claim 1, wherein the method further includes killing attracted whiteflies.

4. A method according to claim 1, wherein the method further includes modifying the behaviour of attracted whiteflies.

5. A method according to claim 1, wherein the method includes controlling whiteflies.

6. A method according to claim 1, wherein linoleic acid is present at a higher concentration than palmitic acid.

7. A method according to claim 1, wherein palmitic acid and linoleic acid are each present at a concentration at least twice that of oleic acid and stearic acid.

8. A method according to claim 1, wherein the fatty acid is provided in a propagator.

9. A method according to claim 8, wherein the propagator is a lure.

10. A method according to claim 9, wherein the lure comprises a matrix and the fatty acid is dispersed within the matrix.

11. A method according to claim 8, wherein the propagator is attached to a whitefly killing device or a whitefly monitoring device.

12. A method according to claim 10, wherein the whitefly killing device or whitefly monitoring device is a trap.

13. A method according to claim 12, wherein trap is selected from a water trap and a trap comprising a substrate and a sticky adhesive coating applied to the substrate, and the substrate or sticky adhesive coating is impregnated with the fatty acid.

14. A method according to claim 1, wherein the fatty acid is provided in a composition comprising an insecticide.

15. A method according to claim 14, wherein the fatty acid is present at a concentration of <0.01 wt % based on total weight of the composition.

16. A method according to claim 1, wherein the method of attracting whiteflies includes attracting whiteflies in a crop growing area.

17. A method according to claim 16, wherein the crop growing area is an enclosed crop growing area.

18. A method according to claim 1, wherein the whiteflies are selected from *Trialeurodes vaporariorum* and *Bemisia tabaci*.

19. A method of attracting whiteflies to a predetermined location, the method comprising the steps of providing a propagator containing a fatty acid composition comprising: a) the combination of palmitic acid, linoleic acid, oleic acid and stearic acid; or b) the combination of octadecenoic acid and eicosatrienoic acid and using said propagator to release $10^{-9}$ g/hr to $10^{-3}$ g/hr of the fatty acid into the air.

20. A method of killing whiteflies, the method comprising the steps of: a) providing a propagator containing a fatty acid composition comprising: a) the combination of palmitic acid, linoleic acid, oleic acid and stearic acid; or b) the combination of octadecenoic acid and eicosatrienoic acid; b) using said propagator to release $10^{-9}$ g/hr to $10^{-3}$ g/hr of the fatty acid composition into the air to attract whiteflies; and c) using a composition or device effective for killing whiteflies to kill attracted whiteflies.

21. A composition for killing whiteflies, the composition comprising a fatty acid composition comprising: a) the combination of palmitic acid, linoleic acid, oleic acid and stearic acid; or b) the combination of octadecenoic acid and eicosatrienoic acid and an insecticide; wherein the fatty acid is present at a concentration of less than 0.05 wt %.

22. A whitefly killing device comprising: a) a fatty acid composition comprising: a) the combination of palmitic acid, linoleic acid, oleic acid and stearic acid; or b) the combination of octadecenoic acid and eicosatrienoic acid; b) a propagator effective for releasing $10^{-9}$ g/hr to $10^{-3}$ g/hr of the fatty acid composition into the air to attract whiteflies; and c) a composition or device for killing attracted whiteflies.

23. A method of treating a crop for whitefly infestation, wherein the method includes the steps of:
  a) providing at least one whitefly killing device comprising: i) a fatty acid composition comprising: a) the combination of palmitic acid, linoleic acid, oleic acid and stearic acid; or b) the combination of octadecenoic acid and eicosatrienoic acid; ii) a propagator effective for releasing $10^{-9}$ g/hr to $10^{-3}$ g/hr of the fatty acid composition into the air to attract whiteflies; and iii) a composition or device for killing attracted whiteflies; and
  b) using said device to attract and kill whiteflies.

24. A device according to claim 22 wherein said device for killing attracted whiteflies comprises a substrate and a sticky adhesive coating applied to the substrate, wherein one or more of the substrate and the sticky coating is impregnated with said fatty acid composition.

25. A device for attracting whiteflies, comprising a fatty acid composition comprising: a) the combination of palmitic acid, linoleic acid, oleic acid and stearic acid; or b) the combination of octadecenoic acid and eicosatrienoic acid and a propagator effective for releasing $10^{-9}$ g/hr to $10^{-3}$ g/hr of the fatty acid composition into the air.

* * * * *